United States Patent
Lingoes et al.

(10) Patent No.: US 9,926,256 B2
(45) Date of Patent: Mar. 27, 2018

(54) CATALYTIC CONVERSION OF LACTIC ACID TO ACRYLIC ACID

(71) Applicant: The Procter & Gamble Company, Cincinnati, OH (US)

(72) Inventors: Janette Villalobos Lingoes, Cincinnati, OH (US); Dimitris Ioannis Collias, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/835,187

(22) Filed: Mar. 15, 2013

(65) Prior Publication Data

US 2013/0274514 A1   Oct. 17, 2013

Related U.S. Application Data

(60) Provisional application No. 61/623,054, filed on Apr. 11, 2012.

(51) Int. Cl.

| | | |
|---|---|---|
| *B01J 27/00* | (2006.01) | |
| *C07C 51/48* | (2006.01) | |
| *B01J 27/18* | (2006.01) | |
| *B01J 27/187* | (2006.01) | |
| *B01J 27/25* | (2006.01) | |
| *C07C 51/377* | (2006.01) | |
| *C07C 51/09* | (2006.01) | |
| *C07C 57/04* | (2006.01) | |
| *A61F 13/534* | (2006.01) | |
| *C08F 2/10* | (2006.01) | |
| *B01J 27/16* | (2006.01) | |
| *B01J 27/185* | (2006.01) | |
| *B01J 27/186* | (2006.01) | |
| *B01J 27/188* | (2006.01) | |
| *B01J 27/195* | (2006.01) | |
| *B01J 27/198* | (2006.01) | |
| *B01J 35/02* | (2006.01) | |
| *B01J 37/00* | (2006.01) | |
| *B01J 37/04* | (2006.01) | |
| *B01J 37/08* | (2006.01) | |
| *C07C 51/44* | (2006.01) | |
| *A61F 13/53* | (2006.01) | |

(52) U.S. Cl.
CPC ............ *C07C 51/48* (2013.01); *A61F 13/534* (2013.01); *B01J 27/16* (2013.01); *B01J 27/1806* (2013.01); *B01J 27/186* (2013.01); *B01J 27/187* (2013.01); *B01J 27/188* (2013.01); *B01J 27/1811* (2013.01); *B01J 27/1817* (2013.01); *B01J 27/1853* (2013.01); *B01J 27/1856* (2013.01); *B01J 27/195* (2013.01); *B01J 27/198* (2013.01); *B01J 27/25* (2013.01); *B01J 35/023* (2013.01); *B01J 37/0036* (2013.01); *B01J 37/04* (2013.01); *B01J 37/08* (2013.01); *C07C 51/09* (2013.01); *C07C 51/377* (2013.01); *C07C 51/44* (2013.01); *C07C 57/04* (2013.01); *C08F 2/10* (2013.01); *A61F 13/53* (2013.01); *A61F 2013/530489* (2013.01); *A61F 2013/530496* (2013.01)

(58) Field of Classification Search
CPC ........................ C07C 51/377; B01J 27/1817
See application file for complete search history.

(56) References Cited

U.S. PATENT DOCUMENTS

| | | |
|---|---|---|
| 2,859,240 A | 11/1958 | Holmen |
| 3,781,222 A | 12/1973 | Weisang et al. |
| 4,521,600 A * | 6/1985 | Wells .................. B01J 27/1802 544/352 |
| 4,695,661 A | 9/1987 | Homann et al. |
| 4,786,756 A | 11/1988 | Paparizos et al. |
| 7,683,220 B2 | 3/2010 | Matsunami et al. |

FOREIGN PATENT DOCUMENTS

| | | |
|---|---|---|
| CN | 200910054519.7 | 7/2009 |
| GB | 1489832 | 10/1977 |
| GB | 2 086 892 A | 5/1982 |

OTHER PUBLICATIONS

International Search Report and Written Opinion for 12426M dated Oct. 8, 2013.
Gunter et al.; J. Catalysis 148:252-260, 1994.
Hong et al.; Appl. Catal. A: General 396:194-200, 2011.
Kirk-Othmer Encylcopedia of Chemical Technology, vol. 1, pp. 324-369, 5$^{th}$ Ed., John Wiley & Sons, Inc., 2004.
Tam et al.; Ind. Eng. Chem. Res: 38:3873-3877, 1999.
Chisolm, Calum R.I. et al., "Engineering the Next Generation of Solid State Proton Conductors: Synthesis and Properties of Ba3—xKxHx(PO4)2", Chem. Mater., vol. 22, No. 3, Feb. 9, 2010, pp. 1186-1194.

* cited by examiner

*Primary Examiner* — Clinton A Brooks
*Assistant Examiner* — Ana Z Muresan
(74) *Attorney, Agent, or Firm* — Brent M. Pebbles

(57) ABSTRACT

Disclosed herein is a mixed phosphate catalyst for converting lactic acid to acrylic acid, which is characterized by a high conversion of lactic acid, a high selectivity for acrylic acid, a high yield of acrylic acid, and correspondingly low selectivity and molar yields for undesired by-products. This is achieved with a particular class of catalysts defined by a mixture of metal-containing phosphate salts. Further, the catalyst is believed to be stable and active for lengthy periods heretofore unseen in the art for such dehydration processes.

6 Claims, 1 Drawing Sheet

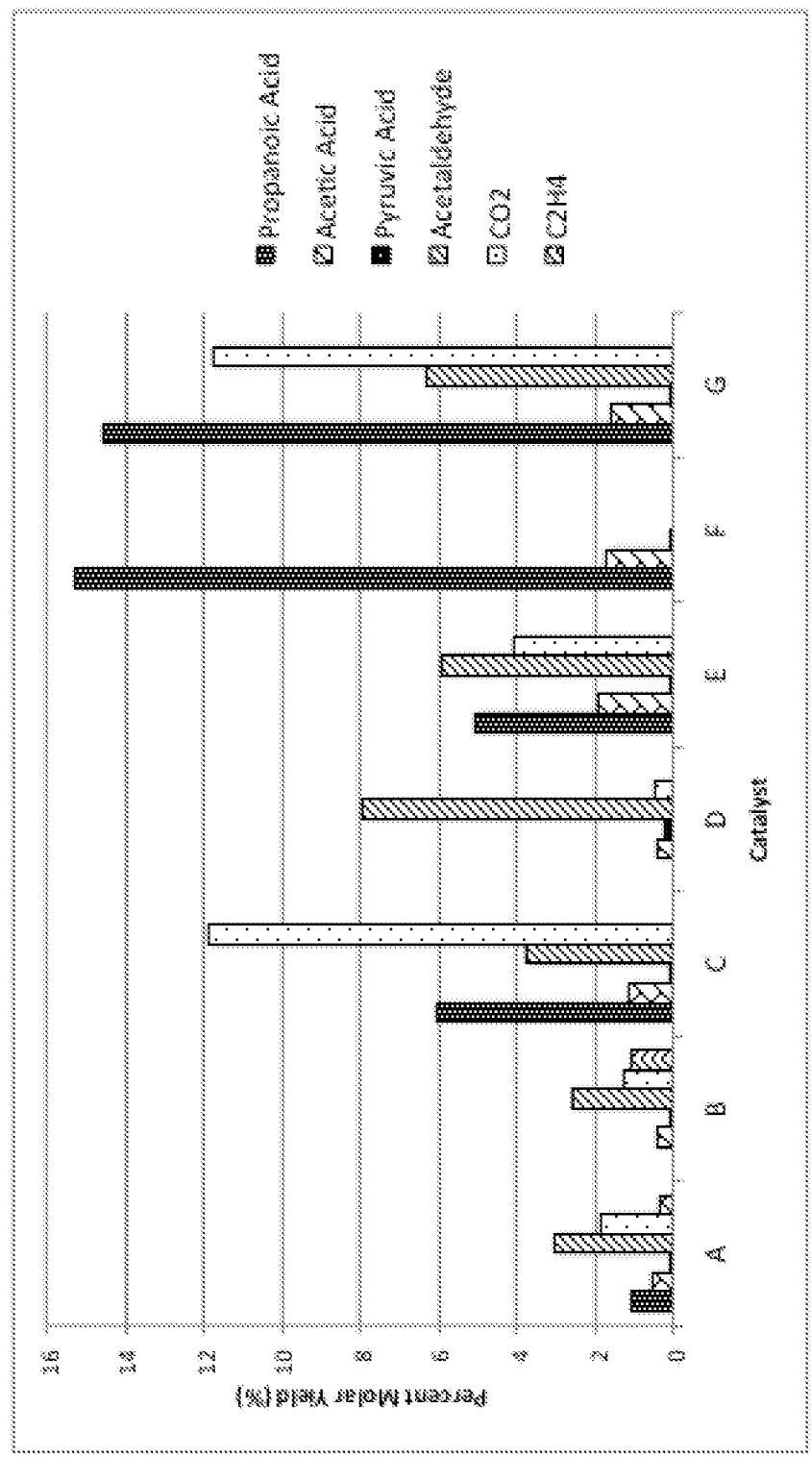

CATALYTIC CONVERSION OF LACTIC ACID TO ACRYLIC ACID

BACKGROUND OF THE INVENTION

Field of the Disclosure

The disclosure generally relates to the conversion of lactic acid to acrylic acid and catalysts useful for the same. More specifically, the disclosure relates to the catalytic dehydration of lactic acid to acrylic acid and the catalysts capable of accomplishing the same without significant conversion of the lactic acid to undesired side products, such as, for example, propanoic and acetic acids.

Acrylic acid has a variety of industrial uses, typically consumed in the form of a polymer. In turn, these polymers are commonly used in the manufacture of, among other things, adhesives, binders, coatings, paints, polishes, and superabsorbent polymers, which are used in disposable absorbent articles including diapers and hygienic products, for example. Acrylic acid is commonly made from petroleum sources. For example, acrylic acid has long been prepared by catalytic oxidation of propylene. These and other methods of making acrylic acid from petroleum sources are described in Kirk-Othmer Encyclopedia of Chemical Technology, Vol. 1, pgs. 342-69 (5$^{th}$ Ed., John Wiley & Sons, Inc., 2004).

Increasingly, however, there is interest in making acrylic acid from non-petroleum based sources, such as lactic acid. U.S. Pat. Nos. 4,729,978 and 4,786,756 generally describe the conversion of lactic acid to acrylic acid. These patents teach that the conversion can be achieved by contacting lactic acid and water with a metal oxide carrier impregnated with a phosphate salt, such as either the monobasic or dibasic potassium phosphate salts $KH_2PO_4$ or $K_2HPO_4$, respectively, or aluminum phosphate. These impregnated carriers are acidic catalysts, and at least the '978 patent emphasizes that the number and strength of the acidic sites on the carrier surface appear to influence the selectivity and conversion to acrylic acid.

Recent research has further focused on modifications to acidic catalysts used to convert lactic acid to acrylic acid. This research has included studies on acidic catalysts (calcium and cupric sulfates) modified with potassium phosphate salts and the effect that reaction temperature and selection of carrier feed gas have on the conversion and selectivity for acrylic acid. See Lin et al. (2008) *Can. J. Chem. Eng.* 86:1047-53. The study reveals, however, that the best molar yield of acrylic acid its researchers were able to obtain was 63.7% and that was only with the aid of carbon dioxide as a carrier gas and contact times (88 seconds) far too high for any practical commercial manufacturing process. More recent research has revealed that phosphate and nitrate salts may desirably change the surface acidity of acidic catalysts to inhibit the decarbonylation/decarboxylation of lactic acid to acetaldehyde, oftentimes an undesired by-product of the conversion. See Huang et al. (2010) *Ind. Eng. Chem. Res.* 49:9082; see also, Weiji et al. (2011) *ACS Catal.* 1:32-41.

Notwithstanding these teachings, however, the data from all of this research still show high amounts of undesired by-products, such as acetaldehyde and propanoic acid. The proximity of the alpha-hydroxyl group relative to the carboxylate group on the lactic acid is believed to be responsible for these by-products, which can also include carbon monoxide, carbon dioxide, 2,3-pentanedione, and oligomers of lactic acid. The by-products can deposit on the catalyst resulting in fouling, and premature and rapid deactivation of the catalyst, as indicated in the publication by Lin et al., for example. Further, once deposited, these by-products can catalyze other reactions undesired of the process, such as polymerization reactions.

Aside from depositing on the catalysts, these by-products—even when present in only small amounts—impose additional costs in processing acrylic acid (when present in the reaction product effluent) in the manufacture of superabsorbent polymers, for example. And the literature regarding the manufacture of these polymers is replete with potential solutions—expensive as they may be—to removing impurities (like acetic acid and propanoic acid) when present among the manufactured acrylic acid in merely small amounts. For example, U.S. Pat. No. 6,541,665 B1 describes the purification of acrylic acid containing propanoic acid, furans, water, acetic acid and aldehydes by crystallization, distillation, and recycling. The '665 patent reports that a 5-stage crystallization (two purification stages and three stripping stages) was effective to obtain 99.94% acrylic acid from a 99.48% acrylic acid mixture containing 2600 parts per million (weight basis) (ppm) acetic acid and 358 ppm propanoic acid, among others. Similarly, U.S. Patent application Publication No. 2011/0257355 describes a method of removing propanoic acid in a single pass crystallization from a crude reaction mixture (containing acrylic acid) derived from glycerol dehydration/oxidation to obtain 99% acrylic acid. These purification methods are necessary to obtain a highly pure acrylic acid necessary for downstream uses in, for example, the manufacture of superabsorbent polymers. Thus, there is certainly value in eliminating impurities, if at all possible, if only to be able to employ these purification methods.

But, heretofore, the manufacture of acrylic acid from lactic acid by processes such as those described in the recent literature noted above, leads to significant amounts of undesired by-products—indeed amounts of by-products far too high to even utilize the purification methods identified in the preceding paragraph. Of course, the low selectivity for acrylic acid in these processes also leads to a loss of feedstock, and ultimately leads to increased production costs. Thus, none of these processes for converting lactic acid to acrylic acid are likely viable commercially.

SUMMARY OF THE INVENTION

It has now been found that acrylic acid can be produced in a high molar yield from lactic acid without the deficiencies noted above. This production of acrylic acid is accompanied by a high conversion of lactic acid, a high selectivity for acrylic acid, and a high yield of acrylic acid, and correspondingly low selectivity and molar yields for undesired by-products. This production is achieved with a particular class of catalysts and employed under certain processing conditions. The result of the process, however, is an acrylic acid product sufficient for conventional industrial uses and one that may not require the complicated purification presently required in the art.

Various embodiments of suitable catalysts are disclosed herein. One embodiment is a mixed phosphate catalyst that includes at least two different phosphate salts selected from the group consisting of Formulas (I), (II), (III), and (IV):

In this embodiment, Z is a Group I metal. Further, in each of Formulas (II) through (IV), each X is independently either a Group I or Group II metal. A number of provisos further define the mixed phosphate catalyst. Specifically, in Formula (II), when X is a Group I metal, a is 0, and when X is a Group II metal, a is 1. Further, in Formula (III), when X is a Group I metal, b is 1, and when X is a Group II metal, b is 0. Still further, in Formula (IV), when X is a Group I metal, c is 2, and when X is a Group II metal, c is 0.

Another embodiment of the mixed phosphate catalyst also includes at least two different phosphate salts. Here, however, one phosphate salt is a precipitation product of phosphoric acid ($H_3PO_4$) and a nitrate salt of Formula (V):

$$X(NO_3)_{2-b} \tag{V}$$

Another of the phosphate salts is selected from the group consisting of Formulas (I), (II), (III), and (IV), set forth above. Variables X and b in Formula (V) are as defined above with respect to Formula (III). More specifically, in each of Formulas (III) and (V), when X is a Group I metal, b is 1, and when X is a Group II metal, b is 0.

In yet another embodiment, the mixed phosphate catalyst again includes at least two different phosphate salts. Here, however, the at least two different phosphate salts are products of a co-precipitation of phosphoric acid ($H_3PO_4$) and two different nitrate salts of Formula (V), as defined above.

These catalysts may be employed in various embodiments of the conversion of lactic acid to acrylic acid. According to one embodiment, a method of making acrylic acid includes contacting with a mixed phosphate catalyst a gaseous mixture that includes water and lactic acid under conditions sufficient to produce acrylic acid in a molar yield of at least 50% from lactic acid. The mixed phosphate catalyst includes a mixture of at least two different phosphate salts, and the mixed phosphate catalyst has a surface acidity density of about 0.35 mmol/m$^2$ or less and a surface basicity density of at least about 2 mmol/m$^2$.

Alternative embodiments of making acrylic acid include the gas-phase catalytic dehydration of lactic acid by contacting a gaseous mixture that includes lactic acid and water with a mixed phosphate catalyst that includes at least two different phosphate salts selected from the group consisting of Formulas (I), (II), (III), and (IV), as defined above. Another embodiment of making acrylic acid includes the gas-phase catalytic dehydration of lactic acid by contacting a gaseous mixture that includes lactic acid and water with a mixed phosphate catalyst that also includes at least two different phosphate salts. But here, at least one phosphate salt is a precipitation product of phosphoric acid ($H_3PO_4$) and a nitrate salt of Formula (V), defined above, and the other phosphate salt is selected from the group consisting of Formulas (I), (II), (III), and (IV), as defined above. In yet another embodiment of making acrylic acid, the method includes the gas-phase catalytic dehydration of lactic acid by contacting a gaseous mixture that includes lactic acid and water with a mixed phosphate catalyst that again includes at least two different phosphate salts. Here, the mixed phosphate catalyst includes at least two different phosphate salts that are products of a co-precipitation of phosphoric acid ($H_3PO_4$) and two different nitrate salts of Formula (V), as defined above.

Additional features of the invention may become apparent to those skilled in the art from a review of the following detailed description, taken in conjunction with the examples, the drawing FIGURES, and the appended claims.

BRIEF DESCRIPTION OF THE DRAWINGS

For a more complete understanding of the disclosure, reference should be made to the following detailed description and sole drawing FIGURE, which graphically illustrates the composition of by-products and amounts of each present in the conversion of lactic acid to acrylic acid according to the Examples set forth below.

While the disclosed catalysts and methods are susceptible of embodiments in various forms, there are illustrated in the FIGURES (and will hereafter be described) specific embodiments of the invention, with the understanding that the disclosure is intended to be illustrative, and is not intended to limit the invention to the specific embodiments described and illustrated herein.

DETAILED DESCRIPTION OF THE INVENTION

Acrylic acid can be produced in a high molar yield from lactic acid without the deficiencies prevalent in the art. This production is accompanied by a high conversion of lactic acid, a high selectivity for acrylic acid, a high yield of acrylic acid, and correspondingly low selectivity and molar yields for undesired by-products. This production is achieved with a particular class of catalysts and employed under certain processing conditions. The result of the process, however, is an acrylic acid product sufficient for conventional industrial uses and one that may not require the complicated purification presently required in the art.

The Catalyst

The functional capabilities of the catalyst in the context of producing acrylic acid from lactic acid are discussed below. The catalyst is generally a mixed phosphate catalyst possessing certain physical characteristics and defined by a particular class of chemicals.

One embodiment of the mixed phosphate catalyst includes at least two different phosphate salts selected from the group consisting of Formulas (I), (II), (III), and (IV):

$$ZH_2PO_4 \tag{I}$$

$$X_{2-a}HPO_4, \tag{II}$$

$$X_3(PO_4)_{2-b} \tag{III}$$

$$X_{2+c}P_2O_7, \tag{IV}$$

In this embodiment, Z is a Group I metal. Further, in each of Formulas (II) through (IV), each X is independently either a Group I or Group II metal. A number of provisos further define the mixed phosphate catalyst. Specifically, in Formula (II), when X is a Group I metal, a is 0, and when X is a Group II metal, a is 1. Further, in Formula (III), when X is a Group I metal, b is 1, and when X is a Group II metal, b is 0. Still further, in Formula (IV), when X is a Group I metal, c is 2, and when X is a Group II metal, c is 0.

Certain embodiments of this catalyst include the phosphate salt of Formula (II), wherein X is potassium (K), the phosphate salt of Formula (III), wherein X is barium (Ba), and/or the phosphate salt of Formula (IV), wherein X is calcium (Ca). Accordingly, the catalyst can include $K_2HPO_4$ and $Ba_3(PO_4)_2$. Alternatively, the catalyst can include $K_2HPO_4$, and $Ca_2P_2O_7$.

Generally, this mixed phosphate catalyst is prepared simply by physically mixing the at least two phosphate salts together and thereafter calcining the mixture, and optional sieving, to form a catalyst suitable for use in converting lactic acid to acrylic acid, as described in further detail below.

Another embodiment of the mixed phosphate catalyst also includes at least two different phosphate salts. Here, however, one phosphate salt is a precipitation product of phosphoric acid ($H_3PO_4$) and a nitrate salt of Formula (V):

$$X(NO_3)_{2-b} \quad\quad\quad (V).$$

Another of the phosphate salts is selected from the group consisting of Formulas (I), (II), (III), and (IV), set forth above. Variables X and b in Formula (V) are as defined above with respect to Formula (III). More specifically, in each of Formulas (III) and (V), when X is a Group I metal, b is 1, and when X is a Group II metal, b is 0.

Certain embodiments of this catalyst include not only the precipitation product noted above, but also the phosphate salt of Formula (II), wherein X is potassium and/or the phosphate salt of Formula (III), wherein X is barium. Accordingly, the catalyst can include $K_2HPO_4$ and the precipitation product of phosphoric acid and $Ba(NO_3)_2$.

Generally, this mixed phosphate catalyst is prepared by mixing an aqueous solution of the nitrate salt with one or more of the phosphate salts and thereafter adding the phosphoric acid and drying the combination of materials to drive off the nitric acid and yield a catalyst product mixture that contains at least two phosphate salts. Following calcining and optional sieving, the mixed phosphate salt is suitable for use in converting lactic acid to acrylic acid, as described in further detail below.

In yet another embodiment, the mixed phosphate catalyst again includes at least two different phosphate salts. Here, however, the at least two different phosphate salts are products of a co-precipitation of phosphoric acid ($H_3PO_4$) and two different nitrate salts of Formula (V), as defined above.

Generally, this mixed phosphate catalyst is prepared by mixing the two nitrate salts with water to form an aqueous solution of the same and thereafter adding the phosphoric acid and drying the combination of materials to drive off the nitric acid and yield a catalyst product mixture that contains at least two phosphate salts. Following calcining and optional sieving, the mixed phosphate salt is suitable for use in converting lactic acid to acrylic acid, as described in further detail below.

In the various embodiments of the mixed phosphate catalysts described above the metals of the different phosphate salts may be the same. Alternatively, the metals may also be different from each other, but when that is the case, then the metals preferably have atomic radii that differ by 30 picometers (pm) or less. For example, when the metals are different, then preferably they are selected from the group consisting of (a) potassium and calcium, (b) lithium (Li) and magnesium (Mg), (c) calcium and barium, (d) sodium (Na) and calcium, and (e) potassium and strontium (Sr).

When the mixed phosphate catalyst includes two different phosphate salts, preferably the two metals are present in a ratio (molar) relative to each other of about 1:9 to about 9:1. For example, when the mixed phosphate catalyst includes dibasic potassium phosphate ($K_2HPO_4$) and a phosphate salt that is a precipitation product of phosphoric acid ($H_3PO_4$) and barium nitrate ($Ba(NO_3)_2$), the potassium and barium preferably are present in a molar ratio, K:Ba, of about 2:3.

The mixed phosphate catalyst may also include a carrier supporting the different phosphate salts. Preferably, the carrier is selected from the group consisting of high and low surface area silica, silica sol, silica gel, alumina, alumina silicate, silicon carbide, diatomaceous earth, titanium dioxide, quartz, diamonds, carbon, zirconium oxide, magnesium oxide, cerium oxide, niobium oxide, and mixtures of the same. More preferably, the carrier is inert relative to the reaction mixture expected to contact the catalyst. In the context of the reactions expressly described herein, therefore, the carrier preferably is a low surface area silica, or zirconium oxide (e.g., zirblast). When present, the carrier is present in an amount of about 5 wt. % to about 90 wt. %, based on the total weight of the catalyst.

The catalyst preferably is calcined at a temperature of about 250° C. to about 450° C. for about one hour to about four hours. More preferably, the catalyst is calcined at 450° C. for four hours (with a 2° C. per minute ramp). The catalyst can be regenerated, as necessary, under similar conditions. Following calcinations, the catalyst is preferably sieved to provide a more uniform product. Preferably, the catalyst is sieved to a median particle size of about 100 micrometers (μm) to about 200 μm. Further, preferably the particle size distribution of the catalyst particles includes a particle span less than about 3, more preferable, less, than about 2, and most preferably, less than about 1.5. As used herein, the term "median particle size" refers to the diameter of a particle below or above which 50% of the total volume of particles lies. This median particle size is designated as $D_{v,0.50}$. While many methods and machines are known to those skilled in the art for fractionating particles into discreet sizes, sieving is one of the easiest, least expensive and common ways to measure particle sizes and particle size distributions. An alternative way to determine the size distribution of particles is with light scattering. As used herein, the term "particle span" refers to a statistical representation of a given particle sample and can be calculated as follows. First, the median particle size, $D_{v,0.50}$, is calculated as described above. Then by a similar method, the particle size that separates the particle sample at the 10% by volume fraction, $D_{v,0.10}$, is determined, and then the particle size that separates the particle sample at the 90% by volume fraction, $D_{v,0.90}$, is determined. The particle span is then equal to $(D_{v,0.90}-D_{v,0.10})/D_{v,0.50}$.

Importantly, it has been determined that the mixed phosphate catalysts described herein are functionally far superior to anything else in the art in the context of the production of acrylic acid due to certain physical characteristics. Specifically, the mixed phosphate catalysts preferably have a surface acidity density of about 0.35 millimoles per square meter (mmol/m²) or less, more preferably about 0.001 mmol/m² to about 0.35 mmol/m². The surface acidity density preferably is measured by ammonia temperature program desorption (ammonia TPD) up to 400° C. in mmol/g and converted to mmol/m² using the catalyst surface area measured by BET (in m²/g). Further, the mixed phosphate catalysts preferably have a surface basicity density of at least about 2 mmol/m², more preferably about 20 mmol/m² to about 100 mmol/m², and even more preferably about 30 mmol/m² to about 80 mmol/m². The surface basicity density preferably is measured by carbon dioxide temperature program desorption ($CO_2$ TPD) up to 400° C. in mmol/g and converted to mmol/m² using the catalyst surface area measured by BET (in m²/g).

Methods of Producing Acrylic Acid

Embodiments of the catalyst described above may be used to produce acrylic acid from a reaction mixture containing lactic acid and water. One specific embodiment of such a process includes contacting with a mixed phosphate catalyst a gaseous mixture that includes water and lactic acid under conditions sufficient to produce acrylic acid in a molar yield of at least 50% from lactic acid. The mixed phosphate catalyst includes a mixture of at least two different phosphate salts, and the mixed phosphate catalyst has a surface acidity density of about 0.35 mmol/m² or less and a surface basicity density of at least about 2 mmol/m². In preferred embodiments, the mixed phosphate catalyst has a surface basicity density of about 20 mmol/m² to about 100 mmol/m², and even more preferably about 30 mmol/m² to about 80 mmol/m². In preferred embodiments, the conditions are sufficient to produce acrylic acid in a molar yield of at least 50% from lactic acid, more preferably at least about 70%, and even more preferably at least about 80%. In other preferred embodiments, the conditions are sufficient to result in a selectivity for acrylic acid of at least about 65%, more preferably at least about 75%, and even more preferably at least about 90%.

Without wishing to be bound by any theory, it is believed that mixed phosphate compounds result in very high surface basicity (i.e., a highly basic catalyst) compared to what a rule of mixtures may have predicted based on the surface basicity density values of the pure phosphate salts, and a highly basic catalyst is responsible for the high acrylic acid yield, high conversion of lactic acid, high selectivity for acrylic acid, and low selectivity for by-products of the conversion common in the art. This is so because reactive intermediates associated with acid-promoted process are avoided or minimized.

The gaseous mixture contacting the catalyst preferably also includes an inert gas, i.e., a gas otherwise inert to the reaction mixture and catalyst under the conditions of the process. The inert gas preferably is selected from the group consisting of nitrogen, helium, neon, argon, and mixtures thereof. More preferably, the inert gas is selected from the group consisting of nitrogen, helium, and mixtures thereof.

Accordingly, the gaseous mixture contacting the catalyst may comprise, upstream of the catalyst separate feeds of carrier gas and a liquid that is made up of an aqueous solution of lactic acid and in certain embodiments derivatives of lactic acid, and one or more of lactide, lactic acid dimer, salts of lactic acid, and alkyl lactates. Lactic acid derivatives include one or more of lactic acid oligomers and polymerization products of lactic acid. Preferably, however, the liquid includes lactic acid, based on the total weight of the liquid, of about 5 wt. % to about 95 wt. %, more preferably about 10 wt. % to about 50 wt. %, and even more preferably about 17 wt. % to about 25 wt. %. Also, preferably, the liquid mixture contains less than about 30 wt. % of lactic acid derivatives, more preferably less than about 10 wt. %, and even more preferably less than about 5 wt. % lactic acid derivatives, based on the total weight of the liquid.

The liquid is combined with the carrier gas at a temperature sufficient to form the gaseous mixture that contacts the catalyst. The conditions under which the gaseous mixture contacts the catalyst preferably include a temperature of about 250° C. to about 450° C., more preferably about 300° C. to about 375° C., and even more preferably about 325° C. to about 350° C. The gaseous mixture preferably includes lactic acid in an amount of about 5 mol. % or less, more preferably about 2.3 mol. % to about 3.5 mol. %, based on the total moles of the gaseous mixture. The amount of lactic acid may be controlled by the amount of carrier gas employed. Specifically, by controlling the gas hourly space velocity (GHSV), one may control the amount of lactic acid in the gaseous mixture contacting the catalyst. Thus, the conditions preferably include a GHSV of about 2200 per hour ($h^{-1}$) to about 7900 $h^{-1}$, more preferably about 3500 $h^{-1}$.

Preferably the process is performed in a reactor that contains an interior surface that is quartz-lined. Alternatively, the process may be performed in a stainless steel (SS) reactor or a reactor constructed of Hastelloy, Inconel, borosilicate, or manufactured sapphire. Preferably the reactor has an aspect ratio (length/diameter) of about 50 to about 100, preferably about 75.

Among the benefits attainable by the foregoing embodiments are the low molar yield of by-products. For example, the conditions are sufficient to produce propanoic acid in a molar yield of less than about 6%, more preferably less than about 1%, from lactic acid present in the gaseous mixture. Similarly, the conditions are sufficient to produce each of acetic acid, pyruvate, 1,2-propanediol, and 2,3-pentanedione in a molar yield of less than about 2%, more preferably less than about 0.5%, from lactic acid present in the gaseous mixture. Similarly, the conditions are sufficient to produce acetaldehyde in a molar yield of less than about 8%, more preferably less than about 4% and even more preferably less than about 3%, from lactic acid present in the gaseous mixture. These are yields believed to be, heretofore, unattainably low. Yet, these benefits are indeed achievable as further evidenced in the Examples set out below.

Alternative embodiments of making acrylic acid include the gas-phase catalytic dehydration of lactic acid by contacting a gaseous mixture that includes lactic acid and water with a mixed phosphate catalyst that includes at least two different phosphate salts selected from the group consisting of Formulas (I), (II), (III), and (IV), as defined above. Another embodiment of making acrylic acid includes the gas-phase catalytic dehydration of lactic acid by contacting a gaseous mixture that includes lactic acid and water with a mixed phosphate catalyst that also includes at least two different phosphate salts. But here, at least one phosphate salt is a precipitation product of phosphoric acid ($H_3PO_4$) and a nitrate salt of Formula (V), defined above, and the other phosphate salt is selected from the group consisting of Formulas (I), (II), (III), and (IV), as defined above. In yet another embodiment of making acrylic acid, the method includes the gas-phase catalytic dehydration of lactic acid by contacting a gaseous mixture that includes lactic acid and water with a mixed phosphate catalyst that again includes at least two different phosphate salts. Here, the mixed phosphate catalyst includes at least two different phosphate salts that are products of a co-precipitation of phosphoric acid ($H_3PO_4$) and two different nitrate salts of Formula (V), as defined above.

EXAMPLES

The following examples are provided to illustrate the invention, but are not intended to limit the scope thereof. Examples 1 through 4 describe the preparation of five different mixed phosphate catalysts in accordance with various embodiments described above. Example 5 describes the preparation of catalysts not according to the invention. Example 6 describes a laboratory scale experiment of converting lactic acid to acrylic acid employing the catalysts described in Examples 1 through 5, and the results thereof. Example 7 describes an experiment to determine the activity of a catalyst according to the invention and reports the data obtained from that experiment. Example 8 describes a laboratory scale experiment of converting lactic acid to acrylic acid employing the catalysts described in Example 1, wherein the reactor material differs. Example 9 describes an experiment performed without catalyst present to demonstrate feed stabilization in a quartz reactor (relative to a stainless steel reactor.

Example 1

An aqueous solution of barium nitrate, $Ba(NO_3)_2$ (85.36 milliliters (ml) of a 0.08 grams per milliliter (g/ml) stock solution, 0.026 mol, 99.999%, from Aldrich #202754), was added to dibasic potassium phosphate, $K_2HPO_4$ (1.517 grams (g), 0.0087 mol, ≥98%, from Aldrich #P3786), at room temperature to provide a white slurry containing potassium (K, M1) and barium (Ba, M2) metals in a M1:M2 molar ratio of 40:60. Phosphoric acid, $H_3PO_4$ (2.45 ml of an 85 wt. %, d=1.684 g/ml, 0.036 mol, from Acros #295700010), was added drop-wise to the slurry. The acid-containing slurry was then dried slowly at 50° C. for 10 hours, then at 80° C. for 10 hours (0.5° C./min ramp) in a vented oven with air flow until full precipitation of the catalyst occurred. Heating continued at 120° C. for 2 hours (0.5° C./min ramp) followed by calcination at 450° C. for 4 hours (2° C./min ramp). After calcination, the catalyst was sieved to about 100 μm to about 200 μm. Two batches of this catalyst were prepared according to the foregoing procedure. The two batches of catalysts are referred to hereinafter as "Catalyst 'A' and Catalyst 'B.'"

Example 2

Sodium phosphate, $Na_3PO_4$ (85.68 g, 0.522 mol, 96% from Aldrich, #342483), was dissolved in 580 ml deionized water and the pH adjusted to 7 with concentrated ammonium hydroxide (general source) as measured by a pH meter. $Ba(NO_3)_2$ (121.07 g, 0.463 mol, 99.999% from Aldrich #202754) was dissolved in 1220 ml deionized water to form a barium nitrate solution. Heating at 35° C. aided dissolution. The barium nitrate solution was added drop wise to the $Na_3PO_4$ solution while stirring and heating to 60° C., forming a white slurry during the addition. The pH was continuously monitored and concentrated ammonium hydroxide added dropwise to maintain pH 7. Heating and stirring at 60° C. continued for 60 minutes, at which time the solid was filtered and washed thoroughly with deionized water. The solid was suspended in 2 L of deionized water and filtered again and washed thoroughly with deionized water. In a vented oven, the filter cake was dried at 120° C. for 5 hours (1° C./min ramp), followed by calcination at 350° C. for 4 hours (2° C./min ramp). After calcination, the barium phosphate was sieved about 100 μm to about 200 μm. The fines were pressed and re-sieved as needed.

The prepared barium phosphate, $Ba_3(PO_4)_2$ (13.104 g, 0.0218 mol), was mixed with dibasic potassium phosphate, $K_2HPO_4$ (1.896 g, 0.0109 mol, from Fisher #P5240/53), which was previously sieved to about 100 μm to about 200 μm, to provide a mixture containing potassium (M1) and barium (M2) metals in a M1:M2 molar ratio of 25:75. The solids were manually mixed and shaken in a closed bottle, followed by heating in a vented oven at 50° C. for 2 hours, at 80° C. (0.5° C./min ramp) for 2 hours, then at 120° C. for 2 hours (0.5° C./min ramp). Thereafter, the catalyst was calcined at 450° C. for 4 hours (0.2° C./min ramp). After calcination, the catalyst was re-sieved to about 100 μm to about 200 μm. This catalyst is referred to hereinafter as "Catalyst 'C.'"

Example 3

Calcium pyrophosphate ($Ca_2P_2O_7$) was prepared according to the procedure described in Hong et al. *Applied Catalysis A: General*, 2011, 396, 194-200. An aqueous solution of calcium chloride hydrate, $CaCl_2.2H_2O$ (39.46 g, 0.268 mol in 100 ml in deionized water), was slowly added (7 ml/min) to a solution of sodium pyrophosphate, $Na_4P_2O_7$ (32.44 g, 0.122 mol, prepared in 250 ml of deionized water by heating at 50° C.) with continuous stirring at room temperature for 1 hour. The resulting white slurry was filtered and dispersed in 350 ml of deionized water twice and filtered again to produce a cake. The cake was dried at 80° C. in a vented oven with air flow for 6 hours, followed by calcination 500° C. for 6 hours. The catalyst was sieved to about 100 μm to about 200 μm.

The prepared calcium pyrophosphate, $Ca_2P_2O_7$ (1.4738 g, 5.80 mmol), was mixed with monobasic potassium phosphate, $KH_2PO_4$ (0.5262 g, 3.87 mmol, from Aldrich), which was previously sieved to about 100 μm to about 200 μm, to provide a mixture containing potassium (M1) and calcium (M2) metals in a M1:M2 molar ratio of 25:75. The solids were manually mixed and shaken in a closed bottle, followed by calcination according to the procedure in described in Example 4. After calcination, catalyst was re-sieved to about 100 μm to about 200 μm. This catalyst is referred to hereinafter as "Catalyst 'D.'"

Example 4 (Comparative)

A number of additional catalysts, referred to herein as Catalysts "E," "F," and "G" were prepared and used for comparative purposes, and those catalysts are described as follows:

A barium phosphate catalyst (Catalyst "E"), not according to the invention, was prepared and used for comparative purposes. Sodium orthophosphate hydrate, $Na_3PO_4.12H_2O$ (19.4566 g, 0.0511 mol, ≥98%, from Aldrich #71911), was dissolved in 125 ml deionized water and heated to 60° C. with heated magnetic stirrer (IKA RCT). $Ba(NO_3)_2$ (19.8866 g, 0.0761 mol, 99.999% from Aldrich) was dissolved in 250 ml deionized water to form a barium nitrate solution. Heating at 35° C. aided dissolution. The barium nitrate solution was added drop wise to the $Na_3PO_4$ solution while stirring at 300 rotations per minute (rpm) and heating to 60° C., forming a white slurry during the addition. The pH of the mixture was monitored using a pH meter. The pH was initially 12.68 and dropped to 11.82 after adding the barium nitrate solution. Heating and stirring at 60° C. continued for 78 minutes, at which time the solid was filtered. The solid was suspended in 250 ml of deionized water and filtered again. This was repeated five times until the final pH was below 9 to obtain a filter cake. In a vented oven, the filter cake was dried at 95° C. for 1 hour, and thereafter at 120° C. overnight, followed by calcination in a kiln at 450° C. for 4 hours (2° C./min ramp). After calcination, the catalyst was sieved to about 100 μm to about 200 μm. This catalyst is referred to hereinafter as "Catalyst 'E.'"

Catalyst "F" was a mixed phosphate catalyst prepared according to Hong et al. *Applied Catalysis A: General*, 2011, 396, 194-200.

Catalyst "G" was a potassium phosphate ($K_2HPO_4$), obtained from Sigma Aldrich, under the product designation "#P3786, ≥98%."

Example 5

Each of catalysts "A" through "K" was employed to convert a reaction mixture containing lactic acid and water to acrylic acid.

Reactor and Analytics

Each of these conversions were carried out in a flow reactor system having temperature and mass flow controllers, and supplied with both a separate liquid and gas feed with a section for mixing. Molecular nitrogen ($N_2$) was fed into the reactor, together with helium (He), which was added as an internal standard for the gas chromatograph (GC) analysis. Aqueous lactic acid (20 wt. % L-lactic acid) was fed to the top of the reactor while controlling the pump pressure (~360 psi) to overcome any pressure drop from the catalyst bed. Stainless steel and, in some cases, quartz reactors with an aspect ratio (i.e., length/diameter) of 75 were used.

Various catalyst beds and gas feed flows were used resulting in a range of space velocities (reported herein). The reactor effluent was also connected to another nitrogen dilution line, which diluted the effluent by a factor of two. The helium internal standard normalized any variation in this dilution for analytical purposes. The condensed products were collected by a liquid sampling system cooled to between 6.5° C. to 10° C. while the gaseous products accumulated on the overhead space of a collection vial. The overhead gaseous products were analyzed using sampling valves and online gas chromatography (GC).

The feed was equilibrated for 1 hour, after which time the liquid sample was collected for 2.7 hours and analyzed at the end of the experiment by offline HPLC. During this time, the gas products were analyzed online twice by GC and reported as an average. Liquid products were analyzed by an Agilent 1200 Series HPLC under the following analytical conditions: Supelcogel-H 250 millimeter (mm) column, eluent isocratic 0.005 M $H_2SO_4$ (aq.), diode-array and refraction index (RI) detectors, runtime: 30 minutes (min), flow: 0.2 ml/min, column temperature: 30° C., RI temperature: 30° C. Gaseous products were analyzed by an Interscience Compact GC using three detectors (one FID and two thermal conductivity detectors "A" and "B," referred to hereinafter as "TCD-A" and "TCD-B," respectively). The gaseous products were reported as an average given by two sequential GC chromatograms.

The TCD-A column was an Rt-Q Bond (Restek, Bellefonte, Pa.), having 26 m in length and an I.D. of 032 mm with a film thickness of 10 μm. There was a pre-column of 2 m. The pressure was set to 150 kPa, with a split flow of 10 mL/min. The column oven temp was set to 100° C. with a vale oven temp of 50° C. The flow was set to 5.0 mL/min, with a carrier gas of helium. The TCD-B column was a Mol sieve MS5A (Restek, Bellefonte, Pa.), having a length of 21 m and a film thickness of 10 μm. There was a pre-column of 2 m. The pressure was set to 200 kPa, with a split flow of 10 mL/min. The column oven temp was set to 70° C. with a vale oven temp of 50° C. The flow was set to 2.0 mL/min, with a carrier gas of argon. The FID column was a RTx-624 (Restek, Bellefonte, Pa.), having a length of 28 m and an inner diameter of 0.25 mm with a film thickness of 14 mm There was a pre-column of 2 m. The pressure was set to 100 kPa, with a split flow to 20 ml/min. The column oven temperature was set to 45° C. with a vale oven temperature of 50° C.

Gas phase calculations were performed on carbon basis; Nml/min=flow rate at standard temperature and pressure; RF=response factor:

CO flow out calculations based on TCD-B data using He as an internal standard:

CO flow out (mmol/min)=[(TCD-B CO Area/TCD-B He Area)*(He flow in (Nml/min))]/22.4

$CO_2$ flow out calculations based on TCD-A using He as an internal standard:

$CO_2$ flow out (mmol/min)=[(TCD-A $CO_2$ Area/TCD-B He Area)*(TCD-A RF $CO_2$)*(He flow in (Nml/min))]/22.4

The acetaldehyde (AcH) flow out was determined using the AcH peak area measured in the FID column (FID AcH Area), the He area measured in the TCD-B column (TCD-B He Area), a response factor relating the $CH_4$ on the FID to the He on the TCD-B (RF $CH_4$/He), a relative response factor relating the AcH to $CH_4$ both on the FID column (RRF AcH/$CH_4$), the internal standard He flow per reactor (He flow in), the number of carbons of acetaldehyde (2), and the ideal gas conversion factor (22.4):

Acetaldehyde (AcH) GC flow out (mmol/min)=[(FID AcH Area/TCD-B He Area)*(RF $CH_4$/He)*(RRF AcH/$CH_4$)*(He flow in (Nml/min)]/(2*22.4)

Liquid phase calculations were performed using HPLC area:

Product flow out (mol/min)=[(HPLC Area/HPLC RF (g-1))/HPLC collection time (min)]*[sample dilution/HPLC inj volume]*[sample weight (g)/MW product (g/mol)]

Liquid Mass Balance (%)=[liquid product weight/LA weight in]*100

Total flow out was calculated on a total carbon basis:

Total Flow Out (mol/min): (2/3)*[$C_2H_4$ flow out (mol/min)]+(2/3)*[$C_2H_6$ flow out (mol/min)]+[$C_3H_6$ flow out (mol/min)]+[$C_3H_8$ flow out (mol/min)]+(2/3)*[AcH flow out (mol/min)]+(4/3)*[$C_4$ flow out (mol/min)]+[LA flow out (mol/min)]+[Pyruvic Acid flow out (mol/min)]+(2/3)*[Acetic acid flow out (mol/min)]+[1,2-propanediol flow out (mol/min)]+[PA flow out (mol/min)]+[AA flow out (mol/min)]+(5/3)*[2,3-pentanedione flow out (mol/min)]+(1/3)*[CO flow out (mol/min)]+(1/3)*[$CO_2$ flow out (mol/min)]

Conversion (%)=[LA flow in (mol/min)−LA flow out (mol/min)]/[LA flow in (mol/min)]*100

Yield (%)=[product flow out (mol/min)/LA flow in (mol/min)]*100

Total molar balance or TMB (%)=[total flow out (mol/min)/LA flow in (mol/min)]*100

Note that feed and product density were accounted for in yield calculations. The acrylic acid yield was corrected to account for variable flow. In most cases this variation was ±5%:

The acrylic acid (AA) yield was corrected for TMB to account for slightly higher or lower flows in the reactor.

AA Yield Corrected to TMB (%): [AA yield/total molar balance]*100

Selectivity (%)=[Yield/Conversion]*100

GHSV=[total gas flow rate/catalyst bed volume].

BET surface area was determined according to ASTM D 4820-99.

Temperature programmed desorption (TPD) was performed on AutoChem II 2920 Chemisorptions Analyzer (Micromeritics, Norcross, Ga.) to get the acidic and basic sites of catalysts. The samples were pretreated at 400° C. for 30 minutes under He. $CO_2$ adsorption was carried out at 40° C. for 30 minutes. $CO_2$ physidesorption was performed at 40° C. for 30 minutes. $NH_3$ adsorption was done at 120° C. for 30 minutes. $CO_2$ and $NH_3$ chemidesorption ramp temperature to 400° C. with 10° C./min and kept the sample to 400° C. for 30 minutes.

Reactor Feed.

A solution (113.6 g) of biomass-derived lactic acid (88 wt. %, from Purac (Lincolnshire, Ill.)) was dissolved in distilled water (386.4 g) to provide a solution with an expected lactic acid concentration of 20 wt. %. This solution was refluxed at 100° C. for 30 hours. The resulting mixture was cooled and analyzed by HPLC (described above) against known weight standards.

Results of the Experiments

Table 5, below, sets forth the GHSV under which the reaction proceeded with each catalyst. All of the reported yields are molar yields (unless indicated otherwise) and were determined after 222 minutes of reaction time. These reactions were carried out in the gas phase and, unless indicated otherwise, employing quartz reactors operating at 350° C., with no support (packing). In the table, "LA" refers to lactic acid; "AA" refers to acrylic acid; "AA Yield" refers to molar yield of acrylic acid from the lactic acid; "PA Yield" refers to the molar yield of propanoic acid from lactic acid; and "N.D." means the value was not determined.

TABLE 1

| Catalyst | LA Conversion (%) | AA Yield (%) | AA Selectivity (%) | PA Yield (%) | GHSV ($h^{-1}$) | BET ($m^2/g$) | Surface Basicity Density ($mmol/m^2$) | Surface Acidity Density ($mmol/m^2$) |
|---|---|---|---|---|---|---|---|---|
| A | 91 | 85 | 93 | 1.1 | 3438 | 0.57 | 77.8 | 0.25 |
| B | 77 | 72 | 92 | 0 | 3438 | 0.40 | 36.1 | 0.18 |
| C | 97 | 41 | 42 | 5 | 3438 | ND | ND | ND |
| D | 65 | 53 | 76 | 0 | 3438 | ND | ND | ND |
| E | 52 | 24 | 48 | 5 | 3544 | 6.9 | 0.82 | 0.15 |
| F | 95 | 21 | 22 | 15 | 2014 | 12.4 | 0.01 | 0.01 |
| G | 98 | 11 | 11 | 15 | 3240 | 2.3 | 4.7 | 0.21 |

The experiment carried out with Catalyst "G" was performed in a stainless steel reactor. The reactor temperature in the experiment carried out with Catalyst "F" was 400° C. The data reported in the table regarding the characteristics (BET, surface basicity and acidity densities) for Catalyst "F" were obtained from Hong et al. *Applied Catalysis A: General*, 2011, 396, 194-200.

The results in Table 5 provide a convenient comparison of the conversion of lactic acid to acrylic acid using catalysts according to the invention (i.e., Catalysts "A" through "D") and those not according to the invention (i.e., Catalysts "E" through "G"). Among other things, under the same or similar reaction conditions, the catalysts according to the invention (i.e., Catalysts "A" through "D") converted more of the lactic acid to acrylic acid than did any of the other catalysts (i.e., Catalysts "E" through "G"). Further, under the same or similar reaction conditions, catalysts according to the invention resulted in a far greater selectivity for acrylic acid and far lower selectivity for propanoic acid than did those catalysts not according to the invention (i.e., Catalysts "E" through "G"). The selectivity is further illustrated relative to other impurities in the sole drawing FIGURE. Catalysts "A" through "D" also had a better performance under these high space velocities, thought to be necessary for feed stabilization. Catalyst "G" or $K_2HPO_4$ had lower selectivity than Catalysts "A" through "D," demonstrating that the presence of both barium and potassium is necessary for high selectivity to acrylic acid.

Table 5, above, sets forth characteristics of five catalysts, and provides a convenient comparison of the surface area, surface basicity density and surface acidity density of catalysts according to the invention (i.e., Catalysts "A" and "B") some not according to the invention (i.e., Catalysts "E" through "G"). The catalysts according to the invention have basicity density values far greater than that of Catalyst "E" alone. Similarly, catalysts "A" and "B" according to the invention have surface acidity density values similar to Catalyst "E." But, the unexpectedly high improvement in basicity of the mixed phosphate catalysts according to the invention, relative to the same densities for a single phosphate catalyst (e.g., Catalyst "E") is believed to have led to the improved conversion of lactic acid and selectivity and yield of acrylic acid from lactic acid. Put another way, the data reflect that catalyst with high surface basicity density performed better than those with lower basicity density. Although the same selectivity was observed for Catalysts "A" and "B," a difference in conversion was observed. That difference is believed to be a result of the number of basic sites per unit area, which was lower for Catalyst "B."

Example 6

An experiment was performed to determine the activity of a catalyst according to the invention. Specifically, Catalyst "B" was subject to 21.6 hours of reaction time under the conditions set forth in Example 6. The data obtained are reported in Table 6, below, wherein acrylic acid yield and selectivity are corrected to TMB, and wherein in the table, "Cony." refers to conversion, and "Select." refers to selectivity.

TABLE 2

| Run Time (Hours) | LA Conversion (%) | AA Yield (%) | AA Select. (%) | PA Select. (%) | Acetic Acid Select. (%) | Acetaldehyde Selectivity (%) | $CO_2$ Select. (%) |
|---|---|---|---|---|---|---|---|
| 2.7 | 75.2 | 66.3 | 88.2 | 0.0 | 0.9 | 5.7 | 1.6 |
| 5.4 | 69.7 | 65.2 | 93.5 | 0.0 | 0.0 | 6.1 | 0.0 |
| 21.6 | 64.5 | 57.6 | 89.4 | 0.0 | 2.4 | 6.9 | 0.0 |

The data show that the catalyst is stable for at least 21.6 hours insofar as the catalyst, over time, does not appear to significantly or detrimentally change relative to acrylic acid yield and selectivity and similarly does not appear to deteriorate relative to the selectivity for undesired by-products, such as propanoic acid, acetic acid, acetaldehyde, and carbon dioxide.

Example 7

Experiments were performed to consider the effect of the reactor material on the conversion of lactic acid to acrylic acid. All runs were performed using the same reactor configuration but only varying the conditions by using either a quartz-lined reactor or a stainless steel (316) reactor. No inert packing was used, the reactor temperature was maintained at 350° C., and the reactor was operated in each run at a GHSV of 3438 h$^{-1}$.

TABLE 3

| Catalyst | AA Yield (%) | LA Conversion (%) | AA Selectivity (%) | Reactor Material |
|---|---|---|---|---|
| A | 58 | 90 | 64 | Stainless Steel |
| B | 33 | 93 | 35 | Stainless Steel |
| A | 85 | 91 | 93 | Quartz |
| B | 72 | 77 | 92 | Quartz |

The data reported in Table 7, above, demonstrate that reactor composition may be important to feed stabilization, although good yields were also observed using either quartz or stainless steel. The data further demonstrate that quartz reactors performed better, between the two types of reactor, in stabilizing the lactic acid feed from decomposition to products such as oligomerization, thus allowing for superior catalyst performance. Although the same selectivity was observed for Catalysts "A" and "B" using quartz, a difference in conversion was observed. Again, this is thought to be a result of the number of basic sites per unit area, which, for Catalyst B," led to an effective lowering in catalyst loading. The difference in Catalyst "A" and "B" performance in a stainless steel reactor is thought to be due to variable feed decomposition.

Example 8

Experiments without catalyst present further demonstrated the effect of feed stabilization in a quartz reactor. Empty reactors were compared to those packed with fused silica (SiO$_2$) (obtained from Sigma Aldrich (St. Louis, Mo.) and Zirblast (obtained from Saint Gobain Zirpro (Le Pontet Cedex, France) in both stainless steel and quartz reactors.

TABLE 4

| Inert Packing | LA Conversion (%) | AA Yield (%) | AA Selectivity (%) | PA Yield (%) | Reactor Material | GHSV (h$^{-1}$) |
|---|---|---|---|---|---|---|
| Empty | 18 | 0.2 | 0 | 0.2 | Quartz | 3453 |
| Empty | 71.7 | 0.2 | 0 | 13.7 | SS | 3453 |
| Fused SiO$_2$ | 25 | 1.4 | 0.05 | 2.9 | Quartz | 3489 |
| Fused SiO$_2$ | 68.6 | 0 | 0 | 13.4 | SS | 3489 |
| Zirblast | 21.8 | 0 | 0 | 0.2 | Quartz | 3489 |
| Zirblast | 70 | 0 | 0 | 13 | SS | 3489 |

The data reported in Table 8, above, reveal that at high space velocities, very little gaseous byproducts were observed. Thus, it was determined that the use of quartz reactors minimized two important side reactions: lactic acid oligomerization and reduction to propanoic acid. This is important to evaluating the true activity of catalysts, here Catalysts "A" and "B."

The foregoing description is given for clearness of understanding only, and no unnecessary limitations should be understood therefrom, as modifications within the scope of the invention may be apparent to those having ordinary skill in the art.

Results of the Experiments

Table 5, below, sets forth the GHSV under which the reaction proceeded with each catalyst. All of the reported yields are molar yields (unless indicated otherwise) and were determined after 222 minutes of reaction time. These reactions were carried out in the gas phase and, unless indicated otherwise, employing quartz reactors operating at 350° C., with no support (packing). In the table, "LA" refers to lactic acid; "AA" refers to acrylic acid; "AA Yield" refers to molar yield of acrylic acid from the lactic acid; "PA Yield" refers to the molar yield of propanoic acid from lactic acid; and "N.D." means the value was not determined.

TABLE 5

| Catalyst | LA Conversion (%) | AA Yield (%) | AA Selectivity (%) | PA Yield (%) | GHSV (h$^{-1}$) | BET (m$^2$/g) | Surface Basicity Density (mmol/m$^2$) | Surface Acidity Density (mmol/m$^2$) |
|---|---|---|---|---|---|---|---|---|
| A | 91 | 85 | 93 | 1.1 | 3438 | 0.57 | 77.8 | 0.25 |
| B | 77 | 72 | 92 | 0 | 3438 | 0.40 | 36.1 | 0.18 |
| C | 97 | 41 | 42 | 5 | 3438 | ND | ND | ND |
| D | 65 | 53 | 76 | 0 | 3438 | ND | ND | ND |
| E | 52 | 24 | 48 | 5 | 3544 | 6.9 | 0.82 | 0.15 |
| F | 95 | 21 | 22 | 15 | 2014 | 12.4 | 0.01 | 0.01 |
| G | 98 | 11 | 11 | 15 | 3240 | 2.3 | 4.7 | 0.21 |

The experiment carried out with Catalyst "G" was performed in a stainless steel reactor. The reactor temperature in the experiment carried out with Catalyst "F" was 400° C. The data reported in the table regarding the characteristics (BET, surface basicity and acidity densities) for Catalyst "F" were obtained from Hong et al. *Applied Catalysis A: General,* 2011, 396, 194-200.

The results in Table 5 provide a convenient comparison of the conversion of lactic acid to acrylic acid using catalysts according to the invention (i.e., Catalysts "A" through "D") and those not according to the invention (i.e., Catalysts "E" through "G"). Among other things, under the same or similar reaction conditions, the catalysts according to the invention (i.e., Catalysts "A" through "D") converted more of the lactic acid to acrylic acid than did any of the other catalysts (i.e., Catalysts "E" through "G"). Further, under the same or similar reaction conditions, catalysts according to the invention resulted in a far greater selectivity for acrylic acid and far lower selectivity for propanoic acid than did those catalysts not according to the invention (i.e., Catalysts "E" through "G"). The selectivity is further illustrated relative to other impurities in the sole drawing FIGURE. Catalysts "A" through "D" also had a better performance under these high space velocities, thought to be necessary for feed stabilization. Catalyst "G" or K$_2$HPO$_4$ had lower selectivity than Catalysts "A" through "D," demonstrating that the presence of both barium and potassium is necessary for high selectivity to acrylic acid.

Table 5, above, sets forth characteristics of five catalysts, and provides a convenient comparison of the surface area, surface basicity density and surface acidity density of catalysts according to the invention (i.e., Catalysts "A" and "B") some not according to the invention (i.e., Catalysts "E" through "G"). The catalysts according to the invention have basicity density values far greater than that of Catalyst "E" alone. Similarly, catalysts "A" and "B" according to the invention have surface acidity density values similar to Catalyst "E." But, the unexpectedly high improvement in basicity of the mixed phosphate catalysts according to the invention, relative to the same densities for a single phosphate catalyst (e.g., Catalyst "E") is believed to have led to the improved conversion of lactic acid and selectivity and yield of acrylic acid from lactic acid. Put another way, the data reflect that catalyst with high surface basicity density performed better than those with lower basicity density. Although the same selectivity was observed for Catalysts "A" and "B," a difference in conversion was observed. That difference is believed to be a result of the number of basic sites per unit area, which was lower for Catalyst "B."

Example 6

An experiment was performed to determine the activity of a catalyst according to the invention. Specifically, Catalyst "B" was subject to 21.6 hours of reaction time under the conditions set forth in Example 6. The data obtained are reported in Table 6, below, wherein acrylic acid yield and selectivity are corrected to TMB, and wherein in the table, "Cony." refers to conversion, and "Select." refers to selectivity.

TABLE 6

| Run Time (Hours) | LA Conversion (%) | AA Yield (%) | AA Select. (%) | PA Select. (%) | Acetic Acid Select. (%) | Acetaldehyde Selectivity (%) | $CO_2$ Select. (%) |
|---|---|---|---|---|---|---|---|
| 2.7 | 75.2 | 66.3 | 88.2 | 0.0 | 0.9 | 5.7 | 1.6 |
| 5.4 | 69.7 | 65.2 | 93.5 | 0.0 | 0.0 | 6.1 | 0.0 |
| 21.6 | 64.5 | 57.6 | 89.4 | 0.0 | 2.4 | 6.9 | 0.0 |

The data show that the catalyst is stable for at least 21.6 hours insofar as the catalyst, over time, does not appear to significantly or detrimentally change relative to acrylic acid yield and selectivity and similarly does not appear to deteriorate relative to the selectivity for undesired by-products, such as propanoic acid, acetic acid, acetaldehyde, and carbon dioxide.

Example 7

Experiments were performed to consider the effect of the reactor material on the conversion of lactic acid to acrylic acid. All runs were performed using the same reactor configuration but only varying the conditions by using either a quartz-lined reactor or a stainless steel (316) reactor. No inert packing was used, the reactor temperature was maintained at 350° C., and the reactor was operated in each run at a GHSV of 3438 $h^{-1}$.

TABLE 7

| Catalyst | AA Yield (%) | LA Conversion (%) | AA Selectivity (%) | Reactor Material |
|---|---|---|---|---|
| A | 58 | 90 | 64 | Stainless Steel |
| B | 33 | 93 | 35 | Stainless Steel |

TABLE 7-continued

| Catalyst | AA Yield (%) | LA Conversion (%) | AA Selectivity (%) | Reactor Material |
|---|---|---|---|---|
| A | 85 | 91 | 93 | Quartz |
| B | 72 | 77 | 92 | Quartz |

The data reported in Table 7, above, demonstrate that reactor composition may be important to feed stabilization, although good yields were also observed using either quartz or stainless steel. The data further demonstrate that quartz reactors performed better, between the two types of reactor, in stabilizing the lactic acid feed from decomposition to products such as oligomerization, thus allowing for superior catalyst performance. Although the same selectivity was observed for Catalysts "A" and "B" using quartz, a difference in conversion was observed. Again, this is thought to be a result of the number of basic sites per unit area, which, for Catalyst B," led to an effective lowering in catalyst loading. The difference in Catalyst "A" and "B" performance in a stainless steel reactor is thought to be due to variable feed decomposition.

Example 8

Experiments without catalyst present further demonstrated the effect of feed stabilization in a quartz reactor. Empty reactors were compared to those packed with fused silica ($SiO_2$) (obtained from Sigma Aldrich (St. Louis, Mo.) and Zirblast (obtained from Saint Gobain Zirpro (Le Pontet Cedex, France) in both stainless steel and quartz reactors.

TABLE 8

| Inert Packing | LA Conversion (%) | AA Yield (%) | AA Selectivity (%) | PA Yield (%) | Reactor Material | GHSV ($h^{-1}$) |
|---|---|---|---|---|---|---|
| Empty | 18 | 0.2 | 0 | 0.2 | Quartz | 3453 |
| Empty | 71.7 | 0.2 | 0 | 13.7 | SS | 3453 |
| Fused $SiO_2$ | 25 | 1.4 | 0.05 | 2.9 | Quartz | 3489 |
| Fused $SiO_2$ | 68.6 | 0 | 0 | 13.4 | SS | 3489 |
| Zirblast | 21.8 | 0 | 0 | 0.2 | Quartz | 3489 |
| Zirblast | 70 | 0 | 0 | 13 | SS | 3489 |

The data reported in Table 8, above, reveal that at high space velocities, very little gaseous byproducts were observed. Thus, it was determined that the use of quartz reactors minimized two important side reactions: lactic acid oligomerization and reduction to propanoic acid. This is important to evaluating the true activity of catalysts, here Catalysts "A" and "B."

The foregoing description is given for clearness of understanding only, and no unnecessary limitations should be understood therefrom, as modifications within the scope of the invention may be apparent to those having ordinary skill in the art.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A mixed phosphate catalyst comprising at least two different phosphate salts, wherein the at least two different phosphate salts comprise $K_2HPO_4$ and $Ba_3(PO_4)_2$, and further, wherein the potassium of the $K_2HPO_4$ and the barium of the $Ba_3(PO_4)_2$ are present in a molar ratio, K:Ba, of about 2:3.

2. The mixed phosphate catalyst of claim 1, wherein the catalyst has been calcined at a temperature of about 250° C. to about 450° C. for about one hour to about four hours.

3. The mixed phosphate catalyst of claim 1 further comprising a carrier supporting the at least two different phosphate salts.

4. The mixed phosphate catalyst of claim 3, wherein the carrier is selected from the group consisting of silica, silica sol, silica gel, alumina, alumina silicate, silicon carbide, diatomaceous earth, titanium dioxide, quartz, diamonds, and mixtures of the same.

5. The mixed phosphate catalyst of claim 1 having a surface acidity density of about 0.35 millimoles per square meter ($mmol/m^2$) or less.

6. The mixed phosphate catalyst of claim 1 having a surface basicity density of at least about 2 $mmol/m^2$.

* * * * *